United States Patent [19]
Caizza et al.

[11] Patent Number: 6,077,259
[45] Date of Patent: Jun. 20, 2000

[54] CONTAMINATION RESISTANT CONNECTOR

[75] Inventors: Richard J. Caizza, Barry Lakes; Michael Carter, Sommerville; Richard L. Griffith, Allendale, all of N.J.

[73] Assignee: Becton, Dickinson and Company, Franklin Lakes, N.J.

[21] Appl. No.: 09/163,963

[22] Filed: Sep. 30, 1998

[51] Int. Cl.[7] .................................................. A61M 25/16
[52] U.S. Cl. ........................ 604/534; 604/905; 604/111; 137/614.04
[58] Field of Search ..................... 137/614.03, 614.04, 137/614.06; 604/533, 534, 537, 905, 167, 110, 111, 535

[56] References Cited

U.S. PATENT DOCUMENTS

| | | | |
|---|---|---|---|
| 4,271,865 | 6/1981 | Galloway et al. | 137/614.06 |
| 5,261,881 | 11/1993 | Riner | 604/110 |
| 5,536,258 | 7/1996 | Folden | 604/265 |
| 5,582,600 | 12/1996 | Loh | 604/283 |
| 5,609,195 | 3/1997 | Stricklin et al. | 141/346 |

*Primary Examiner*—Mark O. Polutta
*Assistant Examiner*—Jeremy Thissell
*Attorney, Agent, or Firm*—Arthur D. Dawson

[57] ABSTRACT

A contamination resistant connector for medical tubing includes a first portion with a first fluid passage therethrough occluded by a covered normally closed first valve and a second portion with a second fluid passage therethrough. The second portion is conjugate to and releasably attachable to the first portion with the second fluid passage also being occluded by a covered normally closed second valve. The first valve and the second valve are both only uncovered and opened so that the first fluid passage and the second fluid passage are fluidly communicatively connected, and closed and covered by the respective selective conjugate engagement and disengagement of the first portion and the second portion.

14 Claims, 11 Drawing Sheets

CONTAMINATION RESISTANT CONNECTOR

FIELD OF INVENTION

The present invention is generally related to medical infusion devices and more particularly to connectors for selectively attaching and detaching a fluid handling device to and from a fluid access device implanted in a patient.

BACKGROUND

Generally speaking, catheters are widely used medical devices. Catheters are used intravascularly, intraperitoneally and to provide drainage or treatment for body cavities. Catheters used intravascularly and intraperitoneally are often left in place for extended periods of time with multiple attachments and detachments of fluid handling devices for administration of fluids. With the advent of managed care, many procedures formerly performed only in clinical settings by skilled practitioners are now being practiced by less skilled, although highly motivated, family members or by the patients themselves in non-clinical locations. Intraperitoneal dialysis is one example of such a procedure. In an intraperitoneal dialysis procedure, a patient has many liters of dialysis fluid introduced into the peritoneal cavity for a residence period. The residence period enables the fluid to acquire materials that would normally be excreted by the kidney. After the residence period the dialysis fluid is withdrawn from the patient's peritoneal cavity. Since the fluid is directly introduced into the patient, and the process is repeated almost daily, if there are any microorganisms transmitted along with the fluid, there is a risk of the patient developing a life threatening infection. Prevention of infection in such procedures is primary concern of practitioners involved in this type of practice.

In many chemotherapy procedures, a patient is infused with materials that are potentially toxic to the person administering the treatment. In such cases, prevention of spills during connection and disconnection of the fluid handling device is important. Prevention of spills is also an important consideration in the administration of radioactive pharmaceuticals. Microbial contamination of fluid handling connections to catheters used for total parental nutrition presents risk to patients already in a weakened state.

There have been many studies of the mechanism of infection with catheters used in many of these treatments. One finding of these studies is that a common source of contaminating microorganisms is finger contact with the connectors. Protocols for attachment and detachment of fluid handling devices to catheters often dictate the practitioner's use of rubber gloves, require wiping the connector's surface clean and other sterile practices. These protocols are often difficult to adhere to even for skilled personnel in clincal settings. When treatments involving the use of catheters is moved to an ambulatory and out-patient setting, the adherence to elaborate infection control protocols becomes even more difficult. As a result of these difficulties, there has been considerable effort to develop connectors for attaching fluid handling devices to catheters that are less prone to contamination.

Another area of infection prevention is development of connectors that are antimicrobial. U.S. Pat. No. 5,536,258 to Folden discloses an antimicrobial tubing connector for medical procedures. The '258 patent teaches that about sixty percent of the continuous ambulatory peritoneal dialysis (CAPD) patients develop peritonitis within two years after starting the treatment. The '258 patent further teaches that there are many protocols and types of connectors that have been developed to address the problem of contamination of connectors used for repeated connections and disconnections of medical fluid transfer procedures. The solution to the connector contamination problem disclosed in the '258 patent is a connector with a recessed male portion and a female portion with "O" rings that form a seal around the recessed male portion. The '258 patent further teaches that an antimicrobial silver coating is applied to one or more of the surfaces of the connector. While the '258 patent recognizes the contamination problems associated with medical connectors, the device disclosed therein still presents exposed mating surfaces when the male portion is disconnected from the female portion.

Another patent, U.S. Pat. No. 5,582,600, to Loh discloses a connector assembly that has a key component and a lid lock component to provide fluid communication between a fluid source and a destination such as a patient. While the teachings of this patent again recognize the contamination problems associated with repeated connections and disconnections of fluid transmission devices to patients, only one side of one part of the disclosed connector is covered when the parts of the connector are disconnected from each other.

Contamination of exposed connectors used with infusion devices when the parts of the connectors are not attached to each other is a present and ongoing problem, particularly for patients that have compromised immune systems. Although the patents listed above have recognized and identified many of the problems of contamination of catheter connectors, the disclosures of these patents do not address the need for a connector for medical fluid transfers that has a valve in each portion of the connector and that substantially prevents exposure of the fluid contact surfaces when the portions of the connector are disconnected. Such a connector is disclosed hereinbelow.

SUMMARY

A contamination resistant connector of the present invention for medical tubing includes a first portion with a first fluid passage therethrough occluded by a covered normally closed first valve and a second portion with a second fluid passage therethrough. The second portion is conjugate to and releasably attachable to the first portion. The second portion second fluid passage also is occluded by a covered normally closed second valve. The first valve and the second valve are both only uncovered and opened so that the first fluid passage and the second fluid passage are fluidly communicatively connected, and closed and covered by the respective selective conjugate engagement and disengagement of the first portion and the second portion.

The connector of the invention enables a substantially drip-free connection and disconnection of a fluid handling device to a patient. When the portions of the device are disconnected, all fluid path surfaces are covered. Studies have shown that the most common source of contamination of fluid handling devices comes during inadvertent finger touches during lapses in adherence to infection control protocols. The connector of the invention substantially prevents these inadvertent contaminations, as well as substantially preventing exposure of practitioners to the material being infused or withdrawn.

DETAILED DESCRIPTION

Figure 1:
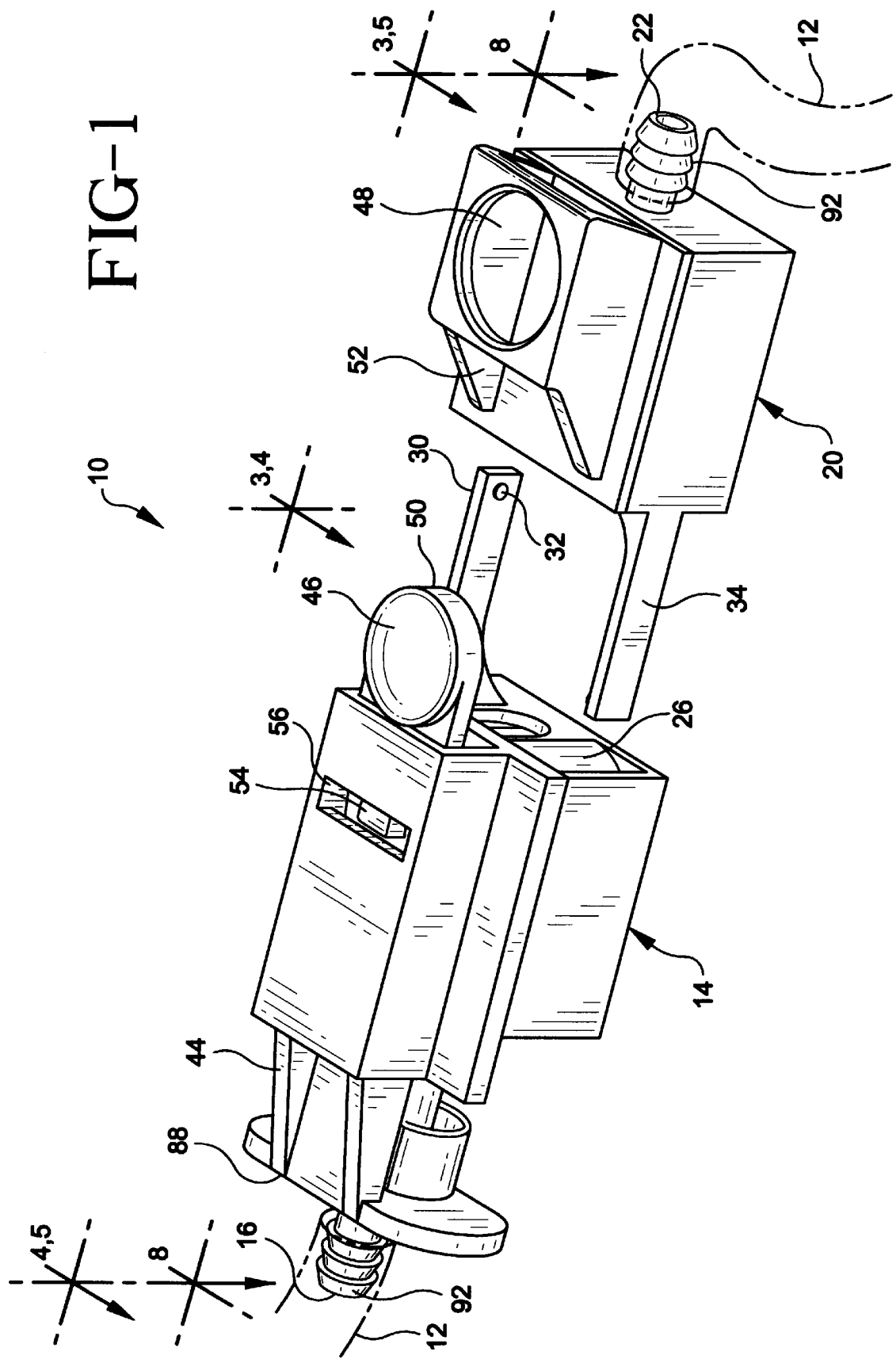
FIG. 1 is a perspective view of the connector of the invention aligned for engagement.

While this invention is satisfied by embodiments in many different forms, there is shown in the drawings and herein described in detail preferred embodiments of the invention with the understanding that the present disclosure is to be considered exemplary of the principles of the invention and is not intended to limit the invention to the embodiments illustrated. The scope of the invention is measured by the appended claims and their equivalents.

Referring to FIGS. 1–11, a contamination resistant connector 10 of the present invention useful for the connection of segments of medical tubing 12 includes a first portion 14 with a first fluid passage 16 therethrough occluded by a covered normally closed first valve 18 and a second portion 20 with a second fluid passage 22 therethrough. Second portion 20 is conjugate to and releasably attachable to first portion 14 with the second fluid passage 22 being occluded by a covered normally closed second valve 24. First valve 18 and second valve 24 are both only uncovered and opened so that first fluid passage 16 and second fluid passage 22 are fluidly communicatively connected, and closed and covered by the respective selective conjugate engagement and disengagement of first portion 14 and second portion 20.

Figure 5:
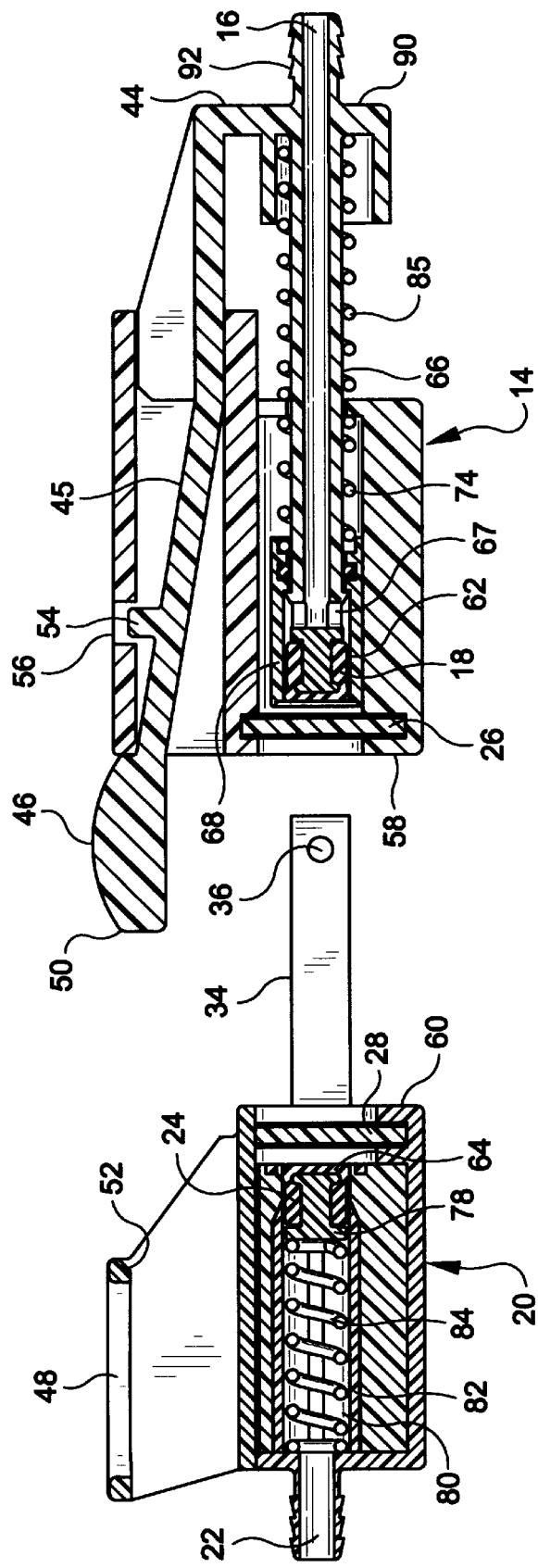
FIG. 5 is a vertical cross-sectional view of the connector the invention as seen in FIG. 1 aligned for engagement taken along the line 5—5.
Figure 7:
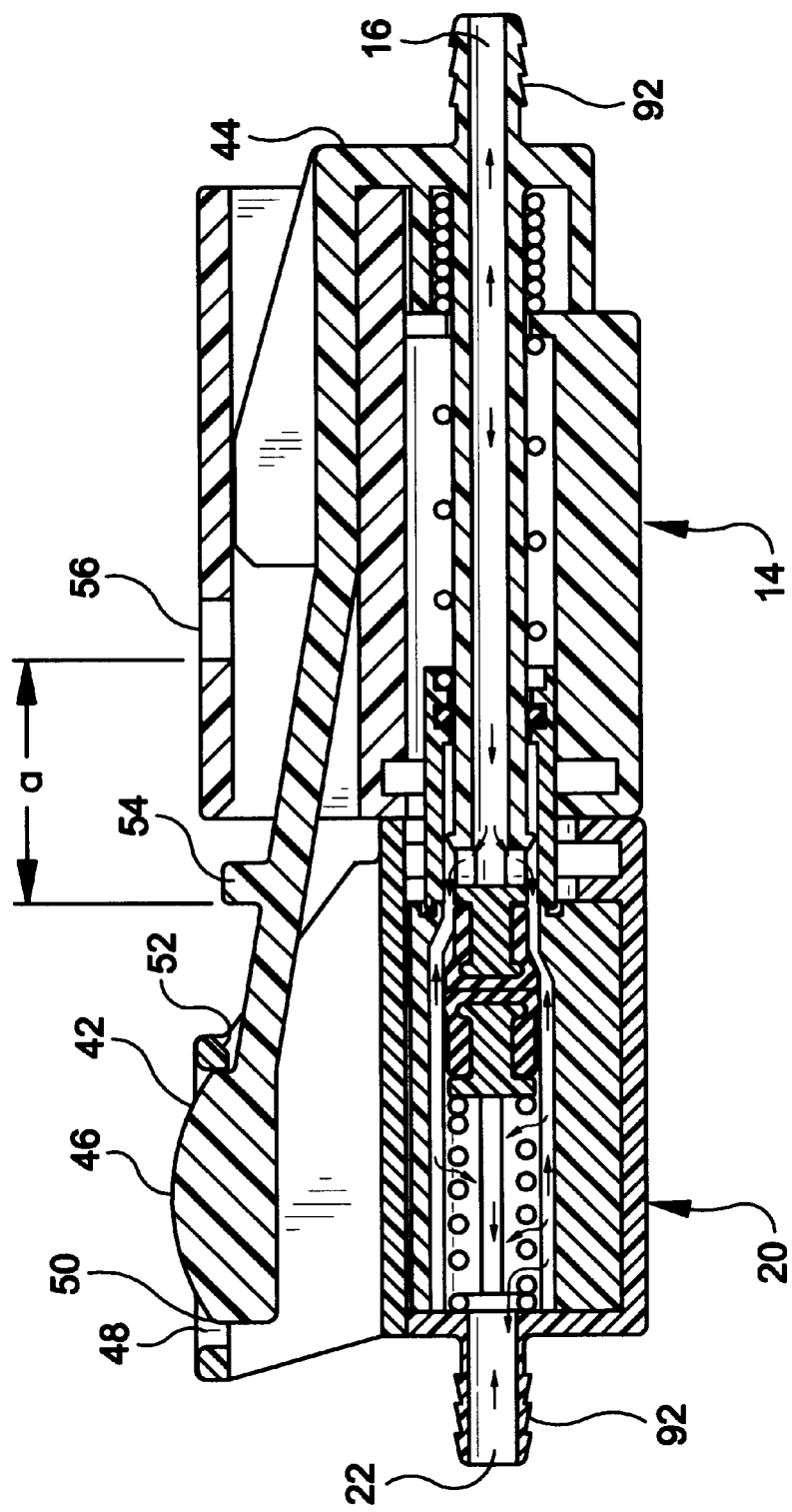
FIG. 7 is a horizontal cross-sectional view of the connector of the engagement in full engagement taken from FIG. 2 along the line 7—7.
Figure 8:
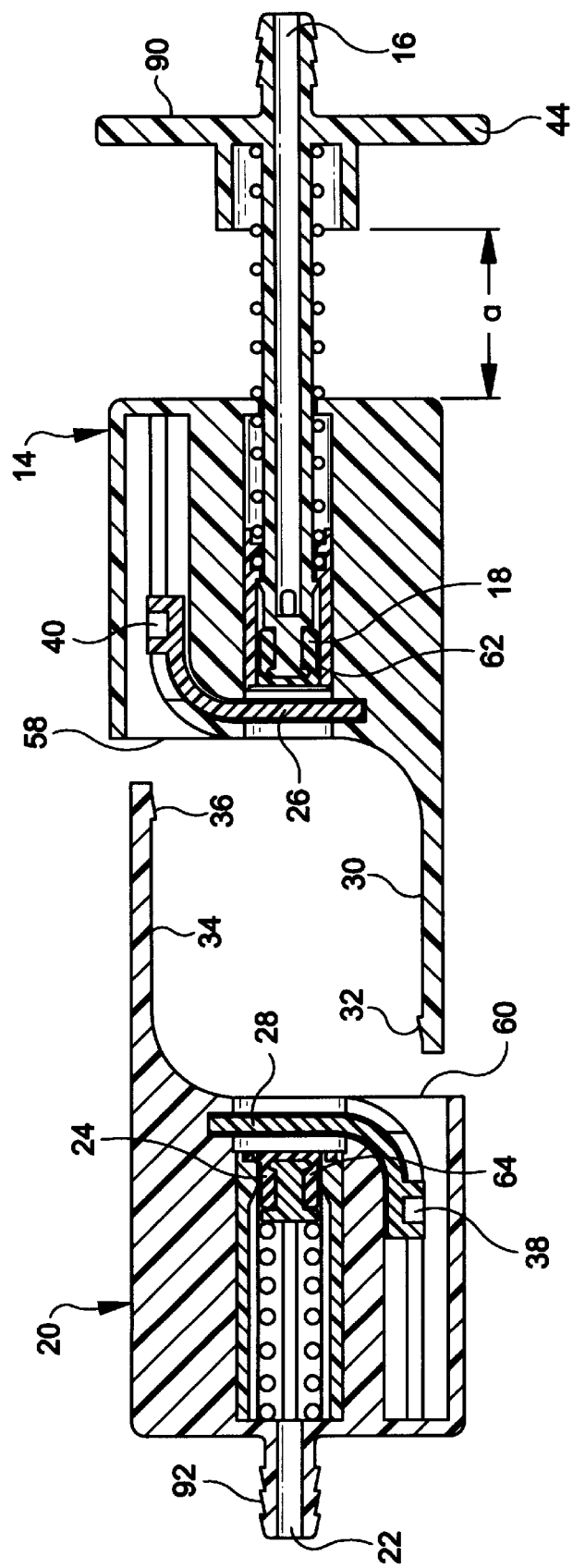
FIG. 8 is a horizontal cross-sectional view of the invention as seen in FIG. 1 taken along the line 8—8.

First valve 18 is covered by a first retractable cover 26 and second valve 24 is covered by a second retractable cover 28 when first portion 14 and second portion 20 are separate from each other as illustrated in FIGS. 1, 5 and 8. First portion 14 has a first outward projection 30 with a protuberance 32 and second portion 20 has a second outward projection 34 with a protuberance 36. Referring now to FIGS. 2, 6, 7, 9 and 10, as first portion 14 and second portion 20 are selectively engaged, protuberance 32 on first outward projection 30 engages a second receptacle 38 on second retractable cover 28 and protuberance 36 on second outward projection 34 engages a first receptacle 40 on first retractable cover 26. As the engagement of first portion 14 and second portion 20 is completed, the respective covers are slidably retracted from the closed positions covering first valve 18 and second valve 24 to open positions, best seen in FIG. 9, where first valve 18 and second valve 24 are respectively uncovered.

Figure 2:
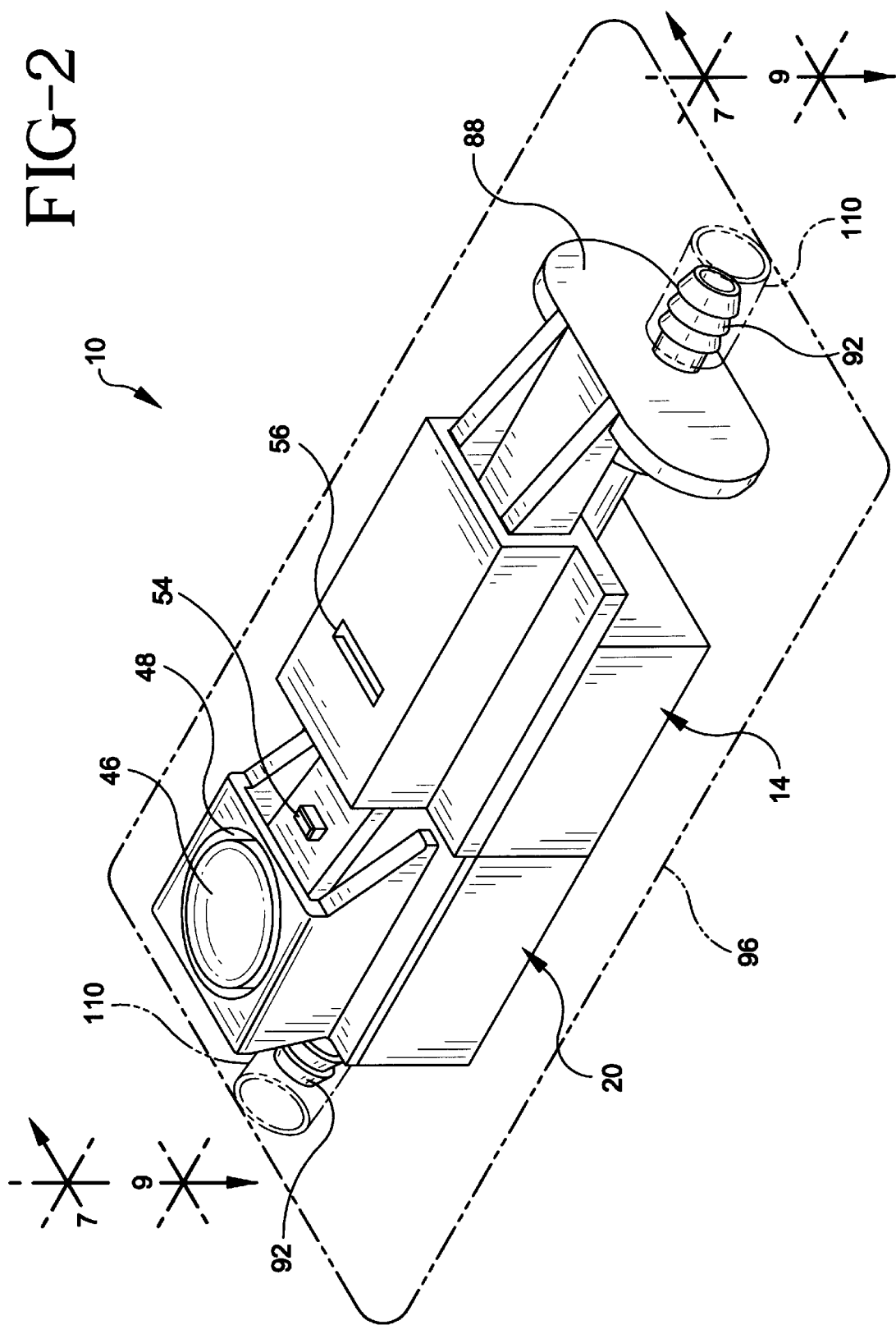
FIG. 2 is a perspective view of the connector of FIG. 1 engaged.
Figure 6:
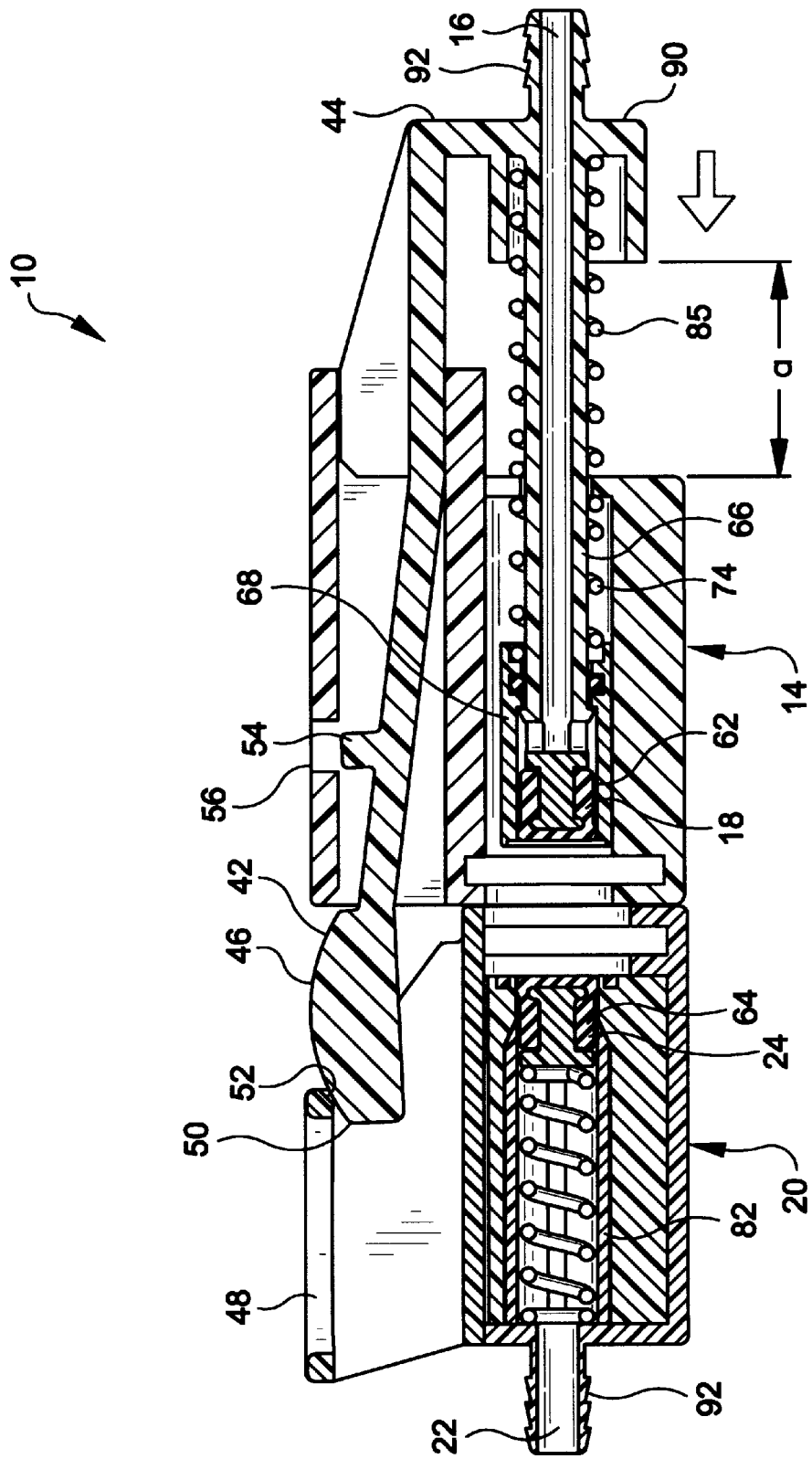
FIG. 6 is a vertical cross-sectional view of the connector of the invention at an intermediate position between full engagement as seen in FIG. 2 and engagement as see seen in FIG. 2.
Figure 9:
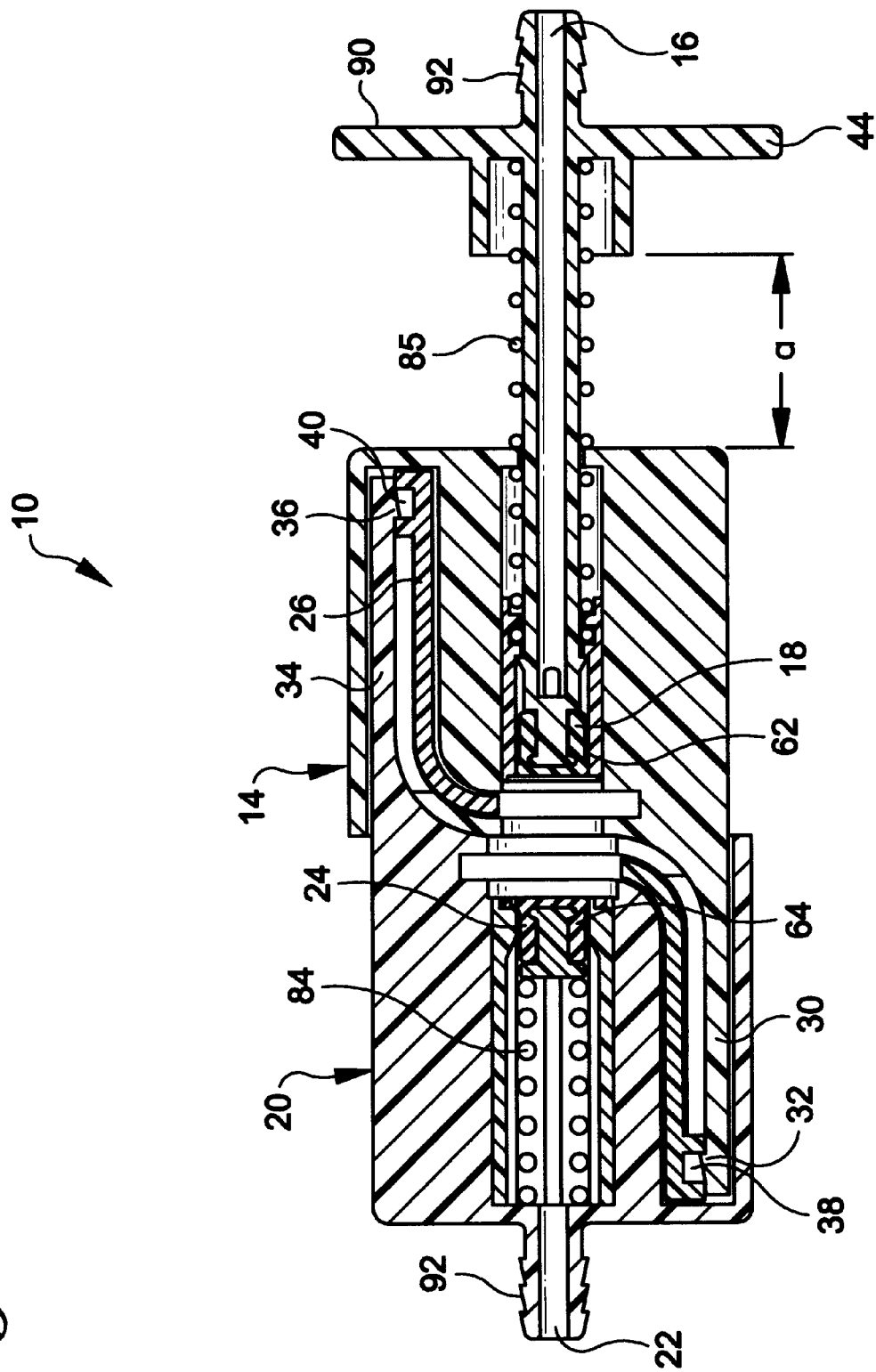
FIG. 9 is a horizontal cross-sectional view of the connector of the invention partially engaged.
Figure 10:
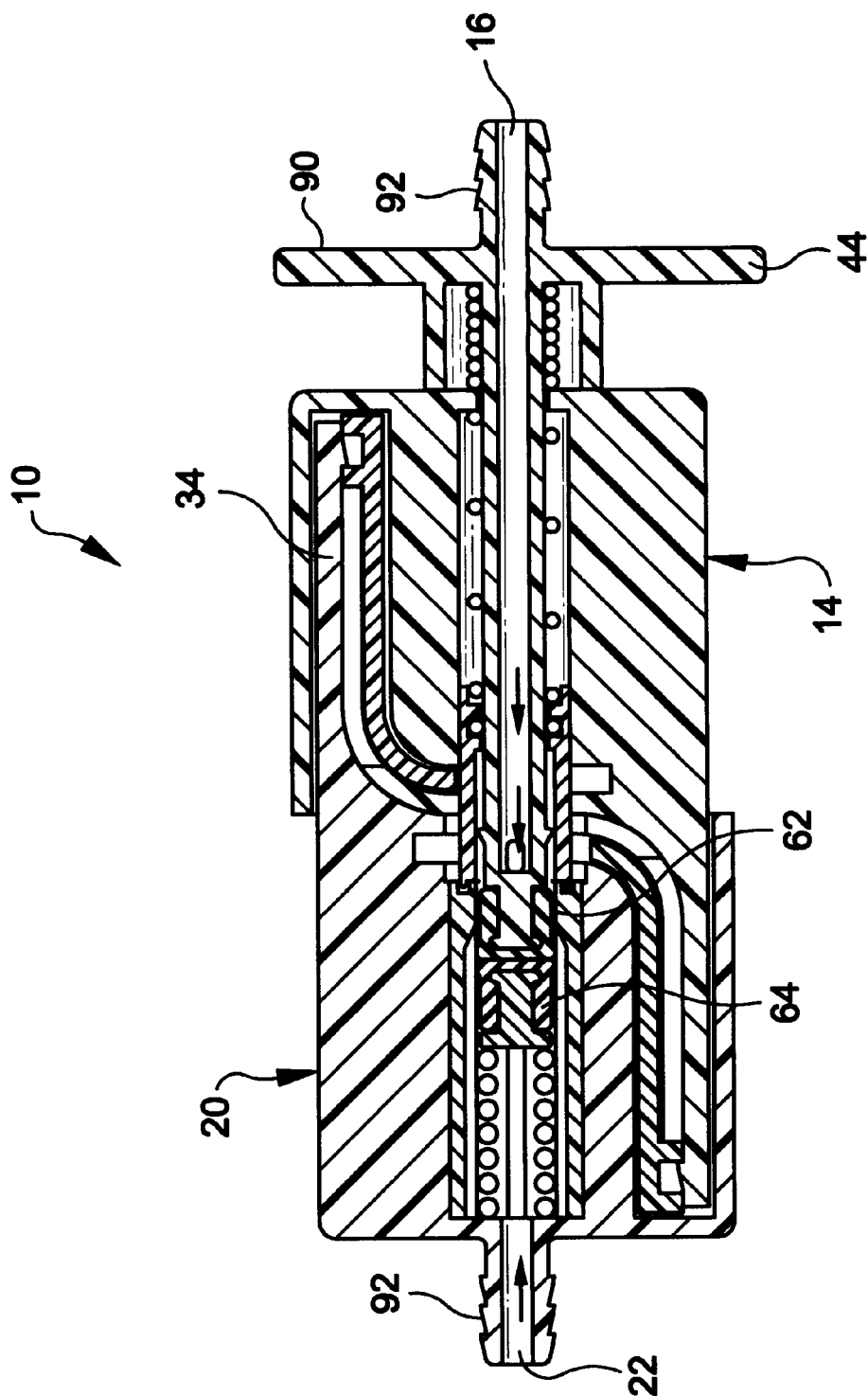
FIG. 10 is a horizontal cross-sectional view of the connector of the invention, analogous to FIG. 9 fully engaged as taken from FIG. 2 along the line 9—9.

Referring now to FIGS. 5, 6 and 7, first portion 14 includes a latch 42 that is coupled to a pusher 44 by a cantilever 45 to allow the practitioner to advance first valve 18 into second portion 20 to engage and to open second valve 24, thereby fluidly to connect first fluid passage 16 to second fluid passage 22 and to releasably engage first portion 14 with second portion 20. Latch 42 preferably has a button member 46 that is disposed to engage releasably an engagement opening 48 in second portion 20 when first portion 14 and second portion 20 are fully engaged and fluid passages 16 and 22 are coupled to allow fluid transmission through connector 10. When first portion 14 and second portion 20 are advanced to full engagement so that a first contact surface 58 and a second contact surface 60 are in contact as shown in FIGS. 6 and 9, a camming surface 52 on second portion 20 engages a follower surface 50 on button member 46 of latch 42. As follower surface 50 engages camming surface 52, button member 46 displaces cantilever 45 from its rest position. Cantilever 45 includes a stop 54 that is disposed to engage a slot 56 in first portion 14 when first portion 14 is detached from second portion 20. When cantilever 45 is displaced from the rest position as follower surface 50 engages camming surface 52, stop 54 is withdrawn from slot 56. When stop 54 is clear of slot 56, the practitioner then advances pusher 44 distance "a" as shown in FIGS. 6, 7, 9 and 10 to position button member 46 in engagement opening 48 and advance first valve 18 into second portion 20 to contact and open first valve 18 and second valve 24 to place first fluid passage 16 in fluid communication with second fluid passage 22. Button member 46 is urged to enter engagement opening by cantilever 45, as shown in FIGS. 2 and 7, to retain first portion 14 and second portion 20 in engagement with first fluid passage 16 and second fluid passage in fluid communication for use. When the practitioner desires to disengage first portion 14 from second portion 20, the practitioner applies sufficient pressure to button member 46 to overcome the bias of cantilever 45 and free button member 46 from engagement opening 48. When button member 46 is free from engagement opening 48, pusher 44 is withdrawn distance "a" to withdraw first valve 18 from second portion 20 thereby closing both first valve 18 and second valve 24. The valve closings occur while first contact surface 58 is still in contact with second contact surface 60, thus the closings of first and second valves 18 and 24 are shielded by the structure of first portion 14 and second portion 20. To complete the selective disengagement, the practitioner then moves first portion 14 and second portion 20 apart. As the portions move away from each other, the respective covers 26 and 28 are slidably moved from their open positions, best seen in FIG. 9, by the withdrawal of first outward projection 30 from second portion 20 and the withdrawal of second outward projection 34 from first portion 14. The slidable movement of covers 26 to the closed positions, best seen in FIG. 8, results in first valve 18 and second valve 24 being respectively covered.

Referring now to FIGS. 3, 4, 8, 9 and 10, first valve 18 includes a first resilient plug 62 and second valve 24 has a second resilent plug 64. When first portion 14 and second portion 20 are separate from each other, first valve 18 is normally closed and covered by first retractable cover 26. First resilient plug 62 is mounted on a movable cannula 66 that has first passage 16 and at least one side port, preferably a plurality of side ports 67, therein. First resilient plug 62 and movable cannula are disposed within a cylinder 68 that forms a seal 70 at one end of cylinder 68 with plug 62. Movable cannula 66 and cylinder 68 are coupled to pusher 44 and biased to a position, best seen FIGS. 4 and 8, where first vale 18 occludes first fluid passage 16. Preferably an auxiliary resilient seal 72 positions movable vannula 66 within cylinder 68, at the other end of cylinder 68. Preferably, auxiliary seal 72 is an "O" ring. A flat washer type seal or gasket formed from a sheet may also be preferred for particular applications. The bias to keep first valve 18 in the normally closed position, is preferably provided by a first valve bias spring 74 that is disposed about movable cannula 66 between the adjacent auxiliary resilient seal 72 and an inside surface 76 of position 14 like. Since movable cannula 66 is coupled to pusher 44, when stop 54 is withdrawn from slot 56 by the engagement of first portion 14 and second portion 20 and the practitioner advance pusher 44 distance "a", movable cannula 66 is concurrently advanced distance "a". The advancement of movable cannula 66 advance first resilient plug 62 into second portion 20 to contact second resilient plug 64 and position side ports 67 to allow fluid flow.

Figure 3:
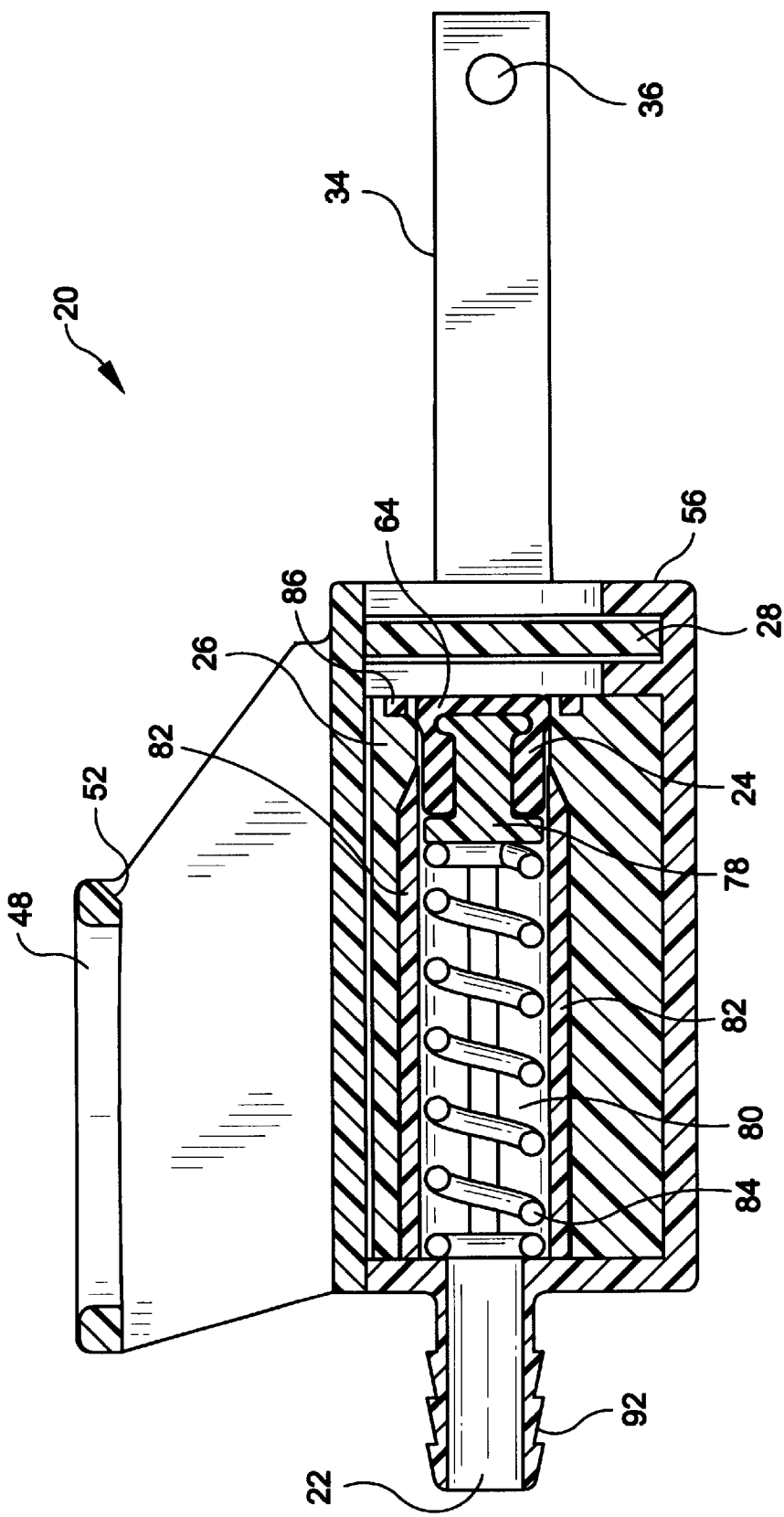
FIG. 3 is a vertical cross-sectional view of the second portion of the connector of FIG. 1 taken along the line 3—3.
Figure 4:
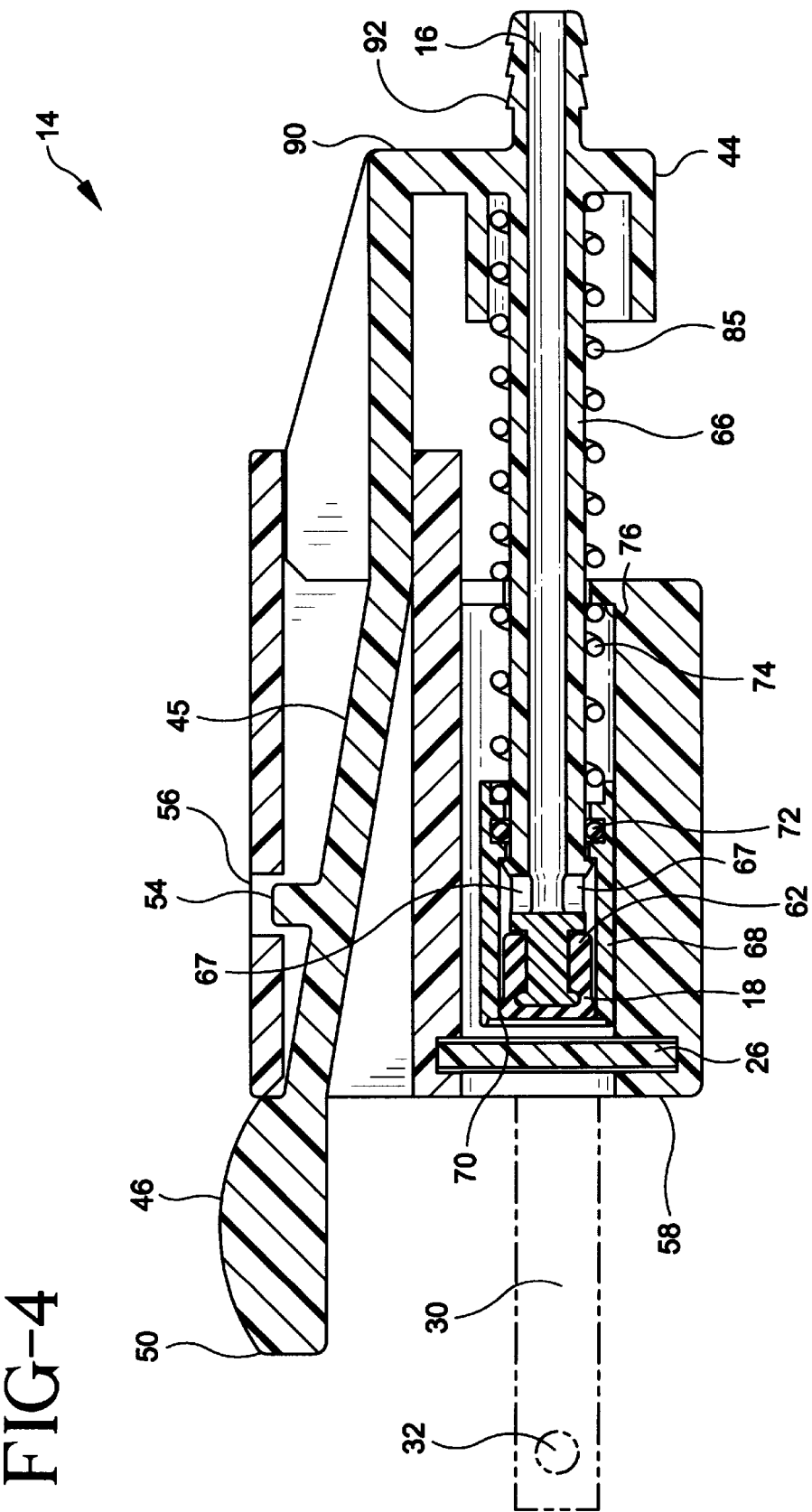
FIG. 4 is a vertical cross-sectional view of the first portion of the connector of FIG. 1 taken along the line 4—4.

Referring now in FIGS. 3 and 8, second valve 24 with second resilient plug 64 is located on a holder 78 within a channel 80 having elongate passages, preferably grooves 82 thereon the defines second fluid passage 22. Channel 80 includes a second vale bias spring 84 that normally keeps second resilient plug 64 beyond grooves 82 to occlude passage 22.

Referring now to FIGS. 6, 7, 9 and 10, as pusher 44 is advanced distance "a", first valve 18 including cylinder 68 and movable cannula 66 are advanced into second portion 20 so that cylinder 68 contacts a secondary seal 86, preferably in the form of an "O" ring or similar resilient seal to provide a substantially leak proof passage for the fluid flow. Once cylinder 68 has formed the seal with secondary seal 86, first resilient plug 62 then contacts second resilient plug 64. With the continued advancement of first resilient plug 62, second resilient plug 64 is then moved to overcome bias spring 84 and expose elongate grooves 82 for fluid flow from second passage 22 into cylinder 68. The advancement of first resilient plug 62 also advances side ports 67 in cannula 66 thereby allowing the fluid flow to continue through cylinder 68 through side ports 67 into first passage 16. The fluid flow through connector 10 is best seen as indicated by the small arrows in FIGS. 7 and 10.

When the selective disengagement of first portion 14 from second portion 20 is desired, the practitioner releases button 46 from engagement opening 48 and retracts pusher 44 distance "a". The retraction of pusher 44 withdraws first resilient plug 62 from contact with second resilient plug 64 and thus allows bias spring 84 to move second resilient plug 64 to close second valve 24 while first resilient plug 62 retracts into first portion 14 and retracts side ports 67 of cannula 66 within cylinder 68. When first resilient plug is retracted into first portion 14, both first fluid passage 16 and second fluid passage 22 are then closed. As the disengagement further proceeds to separation of first portion 14 from second portion 20, first cover 26 and second cover 28 are slidably closed over first valve 18 and second valve 24 respectively by the withdrawal of first outward projection 30 and second outward projection 34 respectively. When the outward projections are fully withdrawn from the opposing portions of the connectors first cover 26 and second cover 28 closed and first projection protuberance 32 and second projection protuberance 36 are withdrawn from first receptacle 40 and second receptacle 38 respectively completing the detachment. Pusher 44 preferably includes an outside bias spring 85 disposed between a finger press 88 that is coupled to pusher 44 and an outside surface 90 of first portion 14 to urge the withdrawal of pusher 44 when button 46 is released from engagement opening 48 and to facilitate the disengagement of first portion 14 from second portion 20.

First portion 14 and second portion 20 each have an attachment, such as a preferably non-releasable tubing fitting 92 for substantially non-releasably attaching medical tubing 12. Other fittings for substantially non-releasably attaching fluid handling devices to connectors may be envisioned, and are considered within the scope of the invention.

Suitable materials for forming the first portion 14 including pusher 44 and cantilever 45, movable cannula 66, cylinder 68 and second portion 20 include, but are not limited to thermoplastic polymeric materials polypropylene, polycarbonate, acrylics, polyamide, polyacetal, acrylonitrile/butadiene/styrene (ABS) and similar. Suitable materials for forming first resilient plug 62 and second resilient plug 64 are elastomeric materials natural rubber, silicone rubber, polychloroprene, ethylene/propylene/diene/ monomer (EPDM) and the like. Auxiliary seal 72 and second seal 86 may be formed from resilient materials such as silicone elastomer, natural rubber, EPDM and the like. Bias springs 74, 84 and 85 are preferably formed from a metallic material such as stainless steel, but for particular applications, a resilient elastomeric material may be suitable.

Preferably, connector 10 is sealed in a package 96, illustrated in phantom in FIG. 2, formed from materials substantially resistant to the passage of microorganisms and exposed to conditions that substantially render any microorganisms in the package nonviable. Alternatively, first portion 14 and second portion 20 each may be individually packaged in a package formed from materials substantially resistant to the passage of microorganisms so that the practitioner may selectively leave second portion 20 attached to the device implanted in a patient and selectively use a fresh first portion 14 for the next desired treatment. Suitable materials for forming package 96 include, but are not limited to paper, polymeric films, non-wovens, metallic foils and composites thereof. Suitable conditions for rendering microorganisms non-viable include chemical sterilants such as ethylene oxide and gaseous hydrogen peroxide, and exposure to ionizing radiation such as gamma or electron beam. When selecting materials for forming connector 10 and package 96, care should be taken to ensure compatibility of the materials with the sterilization techniques being considered.

Figure 11:
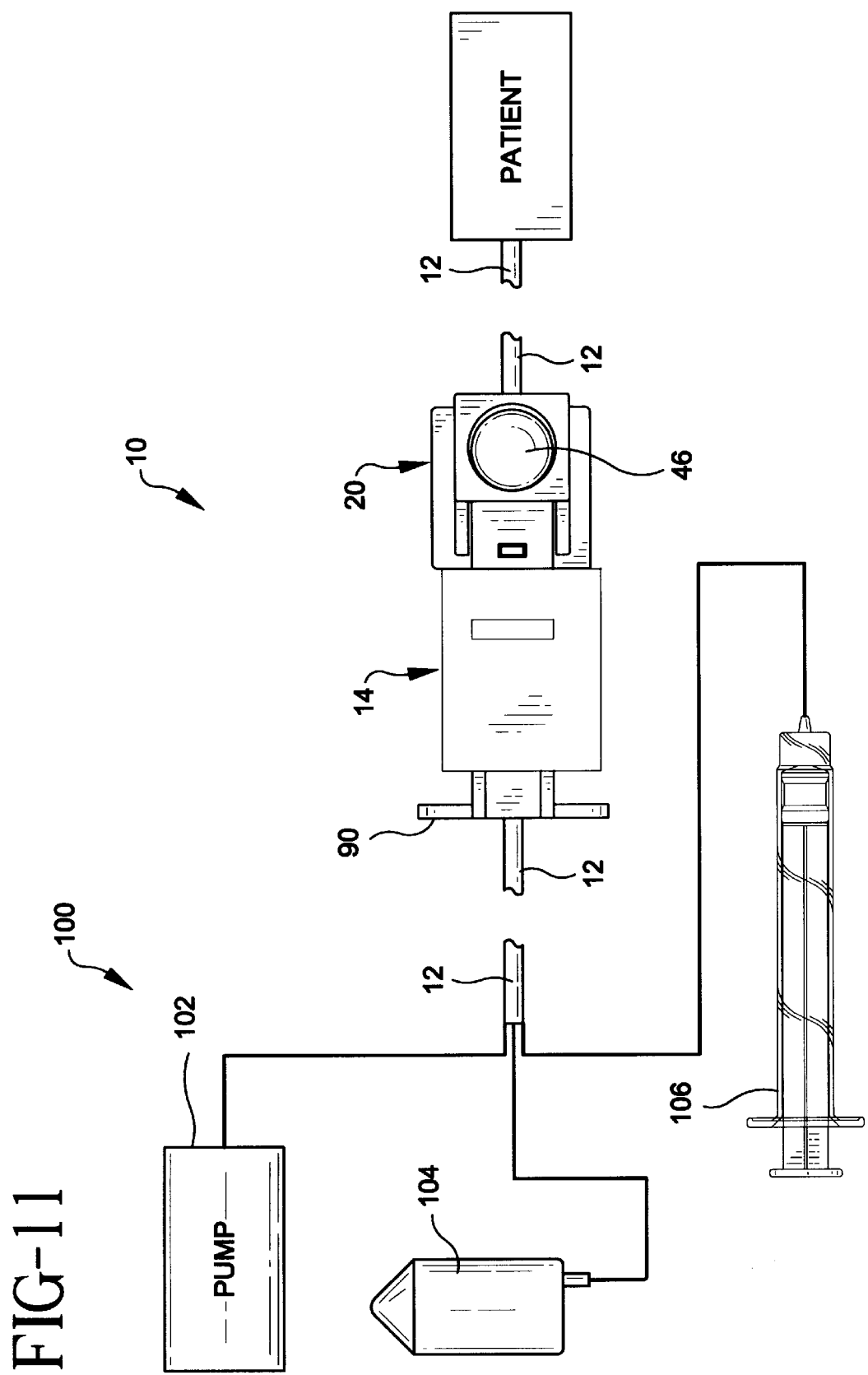
FIG. 11 is a schematic view of a system based on the connector of the invention.

FIG. 11 schematically illustrates a system 100 incorporating connector 10 of the invention. The system may include a pump for medical fluids 102, an infusion bag 104, a syringe 106 or other fluid handling devices that are normally utilized in the medical treatment of patients. Preferably, at least some connectors in system 100 include a tamper-evident cover 110, best seen in FIG. 2 covering tubing fittings 92. A practitioner may selectively attach pump 100 or any other fluid handling device to connector 10 or may choose to utilize several first portions 14 with several different devices and selectively attach and detach a plurality of these devices to a single second portion 20 remaining on the patient for particular applications. Suitable materials for forming tamper evident covers include, but are not limited to, frangible heat shrink films, adhesive backed paper labels, heat staked polymeric covers and other frangible materials known in the medical device art. Connector 10 preferably is physically sized about 1 cm thick with length and width dimension about 5 cm by about 2.5 cm, thus facilitating the patient's comfort as well as reducing the chance for contamination of the catheter or other device being used in the patient's treatment.

Connector 10 and system 100 of the invention address the need for a connector and system for medical fluid handling device attachment to a patient that substantially eliminates the opportunity for contamination by finger touch. As a further benefit, connector 10 of the invention allows substantially drip-free connection and disconnection of fluid handling devices. All of the fluid path surfaces are covered except when the portions of the connector are fully engaged. The connection and disconnection of the connector is intuitive and easy. The connector of the invention should be easily compatible with most clinical and ambulatory outpatient protocols for attachment and detachment of fluid handling devices such as dialysis, chemotherapy and total parental nutrition.

What is claimed is:

1. A contamination resistant connector for medical tubing comprising:

a first portion with a first fluid passage therethrough occluded by a normally closed first valve having a retractable cover thereover;

a second portion with a second fluid passage therethrough, said second portion being conjugate to and releasably attachable to said first portion, said second fluid passage being occluded by a normally closed second valve having a retractable cover thereover; and wherein said first valve and said second valve both only being uncovered and opened so that said first fluid passage and said second fluid passage are fluidly communicatively connected and, disconnected, closed and covered by the respective selective conjugate engagement and disengagement of said first portion and said second portion.

2. The contamination resistant connector of claim 1 wherein said first portion has a latch for releasably engaging said second portion, said latch serving to releasably retain said first portion to said second portion.

3. The contamination resistant connector of claim 2 wherein said latch is coupled to said normally closed valve in said first portion so that as said latch is releasably engaged with said second portion, said first valve in said first portion is advanced into said second portion to engage said second valve thereby opening said second valve to establish a fluid tight communication between said passageway in said first portion and said passageway in said second portion.

4. The contamination resistant connector of claim 3 wherein said first valve in said first portion further comprises a pusher to facilitate said advancement of said first valve into said second portion when said first portion is engaged with said second portion.

5. The contamination resistant connector of claim 4 wherein said first portion includes a retractable first cover and said second portion includes a retractable second cover, said covers substantially preventing access to said valves when said first portion and said second portion are disengaged, said covers being retracted from said valves when said first portion and said second portion are engaged.

6. The contamination resistant connector of claim 5 wherein said first portion includes a first outward projection and said second portion includes a second outward projection, said first projection being disposed to engage said retractable second cover on said second portion and said second outward projection being disposed to engage said first retractable cover on said first portion when said first portion and said second portion are releasably engaged.

7. The contamination resistant connector of claim 6 wherein said first outward projection and said second outward projection each include a protuberance that respectively each releasably engage a receptacle on each of said first retractable cover and said second cover.

8. The contamination resistant connector of claim 7 wherein said first retractable cover and said second retractable cover each are slidably disposed to move from a closed position, wherein said first valve and said second valve respectively are covered when said first portion and said second portion are not engaged, to an open position, when said first portion and said second portion are engaged by said engagement of each of said protuberances with each of said receptacles respectively, wherein a movement of said first portion toward said second portion, as said portions are releasably engaged, urges a sliding motion of each of said covers to said open position, respectively, thereby to uncover each of said valves and, wherein a movement of said first portion away from said second portion, to releasably disengage said first portion from said second portion, urges a sliding motion of each of said covers to said closed position thereby to cover each of said first valve and said second valve respectively.

9. The contamination resistant connector of claim 8 wherein said latch further includes a stop for substantially preventing said first valve from advancing beyond said first portion unless said first portion is engaged with said second portion.

10. The contamination resistant connector of claim 1 wherein said first portion and said second portion each have an attachment for substantially non-releasably attaching a medical tubing in fluid communication with said passageways.

11. The contamination resistant connector of claim 10 wherein at least one of said attachments for substantially non-releasably attaching a medical tubing further includes a removable frangible cover, said frangible cover being substantially not replaceable once removed thereby providing a tamper evidence indication.

12. The contamination resistant connector of claim 1 being sealed in a package formed from materials substantially resistant to the passage of microorganisms and exposed to conditions that render any microorganisms therein substantially nonviable.

13. A system for transmitting a fluid between a fluid handling device and a patient comprising:

a fluid handling device having a tubing attachment and a tubing for delivering and receiving a fluid between said device and the patient;

a contamination resistant connector for connecting said tubing to an implantable device, the connector comprising:

a first portion with a first fluid passage therethrough occluded by a normally closed first valve having a retractable cover;

a second portion with a second fluid passage therethrough, said second portion being conjugate to and releasably attachable to said first portion, said second fluid passage being occluded by a normally closed second valve having a retractable cover; and wherein said first valve and said second valve both only being uncovered and opened so that said first fluid passage and said second fluid passage are fluidly communicatively connected, and disconnected, closed and covered by the respective selective conjugate engagement and disengagement of said first portion and said second portion.

14. The system of claim 13 wherein at least one of said fluid handling device, said tubing attachment, said tubing, said implantable medical device, and said contamination resistant connector further comprises a tamper evident cover.

* * * * *